(12) United States Patent
Tirado Abullon

(10) Patent No.: US 6,499,483 B1
(45) Date of Patent: Dec. 31, 2002

(54) SAFETY CONDOM

(76) Inventor: Salvador Tirado Abullon, C/Ondon de los Frailes 4-3° C, Alicante 03005 (ES)

( * ) Notice: Subject to any disclaimer, the term of this patent is extended or adjusted under 35 U.S.C. 154(b) by 0 days.

(21) Appl. No.: 09/868,548

(22) PCT Filed: Jun. 22, 2000

(86) PCT No.: PCT/ES00/00220
§ 371 (c)(1),
(2), (4) Date: Aug. 30, 2001

(87) PCT Pub. No.: WO01/97723
PCT Pub. Date: Dec. 27, 2001

(51) Int. Cl.$^7$ .................................................. A61F 6/04
(52) U.S. Cl. ........................................ 128/844; 128/918
(58) Field of Search ................................ 128/842, 844, 128/918; 604/347–353

(56) References Cited

U.S. PATENT DOCUMENTS

| | | | | | |
|---|---|---|---|---|---|
| 4,964,416 A | * | 10/1990 | Foldesy | ...................... | 128/842 |
| 5,199,444 A | * | 4/1993 | Wheeler | ...................... | 128/918 |
| 5,454,379 A | * | 10/1995 | Shepherd | ..................... | 128/844 |
| 5,715,839 A | * | 2/1998 | Strauss | ....................... | 128/842 |
| 5,836,307 A | * | 11/1998 | Scholl | ......................... | 128/918 |

\* cited by examiner

*Primary Examiner*—Michael A. Brown
(74) *Attorney, Agent, or Firm*—Merchant & Gould P.C.

(57) ABSTRACT

Safety condom, comprising two compartments, front (2) and back (3), separated and made independent of one another by an interior wall or septum (4) destined to be housed in the sulcus (8) of the penis, establishing a closed front chamber (2) to avoid semen spreading.

5 Claims, 4 Drawing Sheets

SAFETY CONDOM

DESCRIPTION

The present invention is related to the new safety condom, which has general application as a safety contraceptive and medical application preferably to prevent sexually transmitted diseases, as well as other specific diseases, is structurally based on the presence of two compartments, one at the front and the other at the back, both being shaped, separated and made independent of one another by a wall or septum.

BACKGROUND OF THE INVENTION

Up to the present, conventional condoms present a plurality of defects and problems. Among them are partial or total detachment when the penis becomes flaccid, after ejaculation, and as a consequence of this, the condom may even be lost on the floor, in the vagina, etc., with the resulting spreading of the seminal fluid, causing associated risks.

With the structural concept of the new safety condom which is the object of the present invention, all of the defects and problems of the conventional condom are overcome, its primary and most noteworthy characteristic being its total margin of safety.

DESCRIPTION OF THE INVENTION

The new safety condom, object of the present invention, is structurally determined by the presence of two compartments in one body of the configuration of the condom, made of elastic material, preferably latex, variable in all its components, the front and back compartments of which are separated and made independent by a wall or septum.

This wall or septum is located in the body of the condom, and presents a centrally located opening ring.

The diameter of the opening of this ring must necessarily be smaller than the diameter of the opening of the body of the condom.

The smaller diameter circular ring, located in centre of the wall or septum, is situated concentrically in relation to the circle that makes up the outer contour of the body of the condom. In its opening circle or contour, this ring may present another ring or lining which is variable along all its circular edge with the objective of achieving a comfortable, secure and tight fit onto the sulcus, behind the corona of the glass penis.

This ring surrounds the glans penis, which blocks the flow of seminal fluid from the front to the back compartment end simultaneously prevents this condom from coming off from either an erect or a flaccid penis.

In turn, the wall or septum may present an inclination corresponding to the anatomic obliquity of the sulcus and the corona of the glans penis, so as to achieve an ideal fit without causing discomfort, irritation nor inconvenience, and to offer a safe and comfortable condom.

Another structural possibility for the wall a septum may be the perpendicular presentation of the plane that contains the septum with respect to the central lengthwise axis of the body of the condom, achieving the anatomic obliquity once the condom is applied for use, given the elasticity of its components, that is, the angle that would be formed between the septum and this axis would vary between 0 and 45 °.

DESCRIPTION OF THE DRAWINGS

In order to facilitate a better understanding of this description and as an integrated part of the same, a series of figures are attached which, as a non-limitative illustration, represent the following.

PREFERRED EMBODIMENT OF THE INVENTION

Figure 7:
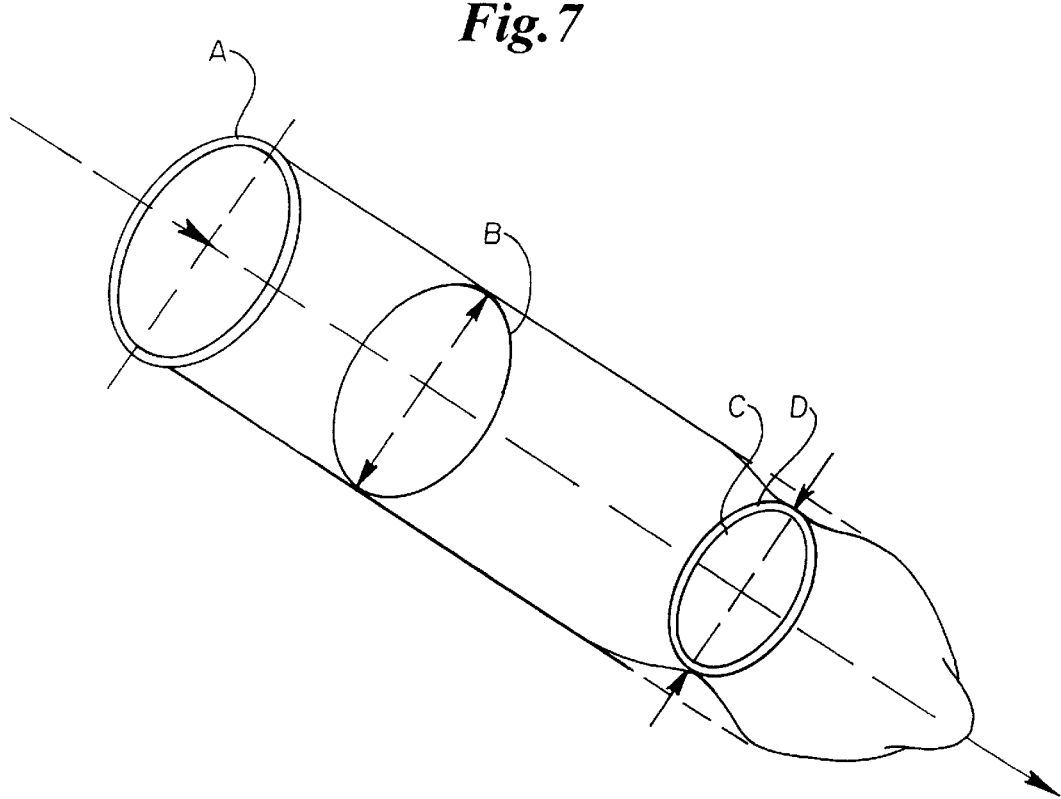
FIG. 7 shows a perspective view of the condom as a practical example just as it would sit once fitted into position.

As can be seen in FIG. 7, a non-limiting extensive example of practical development of the present invention is described.

Basically, the new safety condom, object of the present invention, is structurally characterised by the presence of two compartments, a front compartment and a back one. They are both shaped, separate and made independent of one another by a wall or septum.

This wall or septum, located inside the body of the condom, although not obligatorily, presents a centrally situated opening ring.

The diameter of the opening of this ring must necessarily be smaller than the diameter of the opening of the body of the condom.

The circular ring with the smaller diameter, located centrally within the wall or septum, is situated concentrically in relation to the circle that makes up the outer contour of the body of the condom. In its opening circle or contour this ring may present a thickening ring that is variable around the whole of its circular edge, with the objective of achieving a tight, comfortable and safe fit onto the sulcus, behind the corona of the glans penis.

The wall or septum presents in its structure a perpendicularity with an angle of approximately 90° with respect to the lengthwise central axis of the body of the condom, achieving anatomical obliquity once the condom is applied for use, given the elasticity of its components, the angle being or structurally from 0° to 21.5/23.5° once applied for use.

Likewise the wall or septum may be shaped, with a ring only located centrally, remaining located within the body of the preservative without solution of continuity, making up the two chambers or compartments, front and back.

However, not obligatorily, the shaping, separation and independence of the two chambers are a result of the internal location of the wall or septum within the body of the condom.

If the back chamber should be rooted in the very shaping of the opening ring, the object of the present invention would not vary structurally, being characterised by the presence of the two compartments, front and back, although in this case the wall or septum would remain in an external position, periferically making up the back wall of the front chamber surrounding the corona of the glans penis and achieving, through the elasticity of the opening ring, an adequate fit to the anatomical obliquity of the sulcus.

Figure 2:
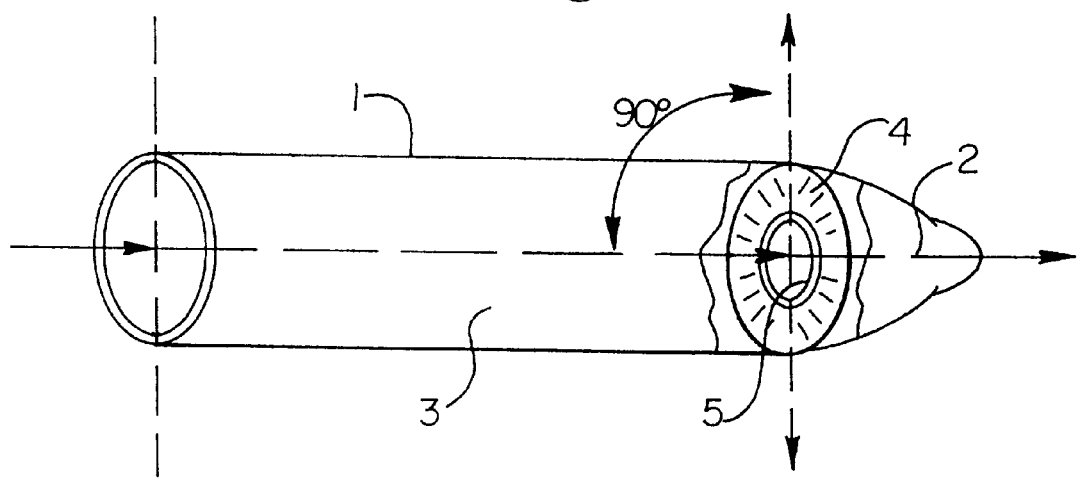
FIG. 2 shows a perspective view of the unrolled condom, in which the wall or septum remains located internally at an angle ($\alpha$) equal to 0.

In FIG. 2, the central ring (3) of the wall or septum (4) must obviously have a smaller diameter than that of the outer contour of the body (1). The difference between the two determines the dimensions of the septum (4).

Likewise, the wall or septum (4), including its centrally based opening ring (5), is to be situated inside a body of the condom without solution of continuity, making up the two chambers or compartments, front (2) and back (3).

Although not necessarily, the shaping, separation and independence of the chambers result from the internal location of the wall or septum (4) within the body of the condom (1).

Figure 5:
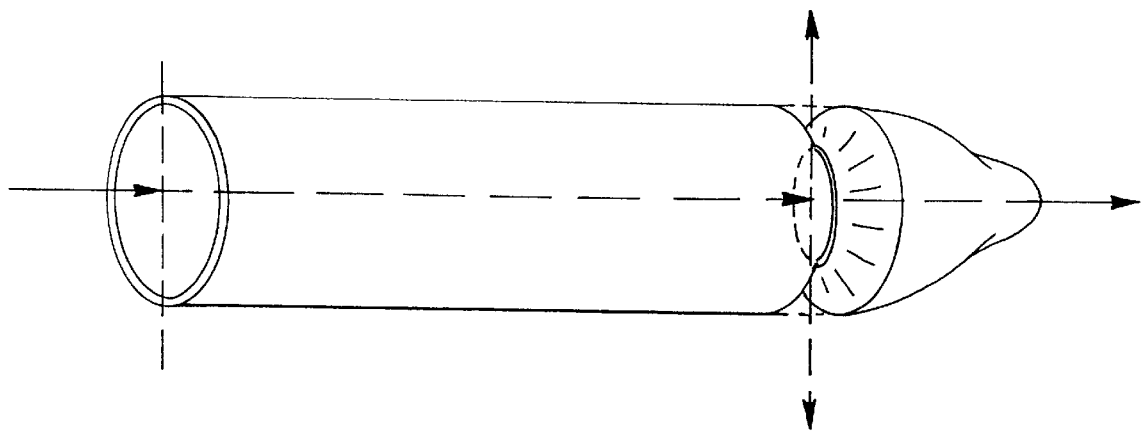
FIG. 5 shows a perspective view of the condom in the wall of septum is located externally.
Figure 6:
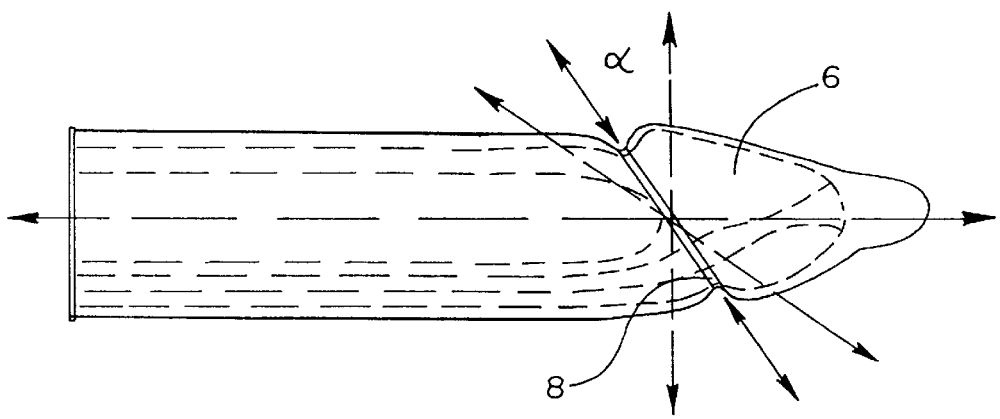
FIG. 6 shows a perspective view of the condom fitted on the penis where the anatomical obliquity of the corona and the sulcus is represented.

If the back chamber (3) should be rooted in the circle that makes up the opening ring (5), there is no structural variation in the object of the invention, in which the presence of the two bodies, front (2) and back (3) is limited or separated by the presence of a wall or septum (4), which is located externally (FIG. 5), peripherally making up the back wall of the front chamber (2), surrounding the corona of the glans penis (6) and achieving, through the elasticity of the opening ring (5), an adequate fit to the anatomic obliquity of the sulcus (8) (see FIG. 6).

Figure 1:
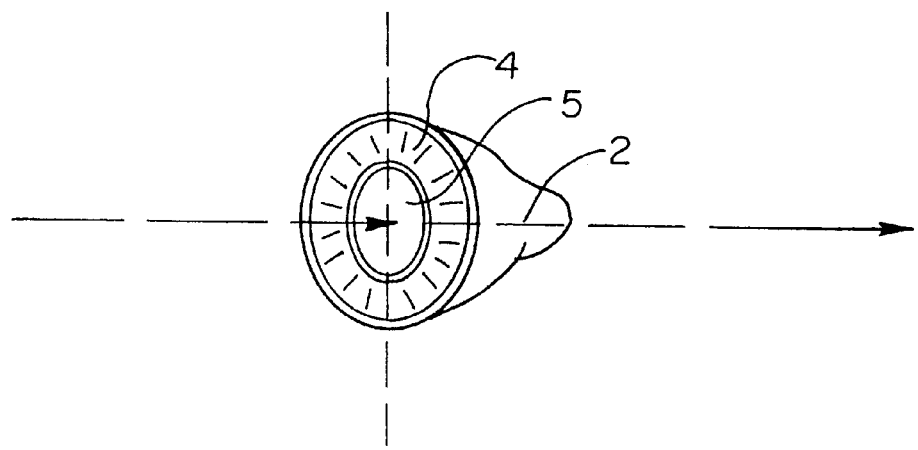
FIG. 1 shows a perspective view of the condom in rolled-up condition.

In FIG. 1, the new safety condom can be seen, as presented for use, folded and rolled into the back chamber (3).

Figure 3:
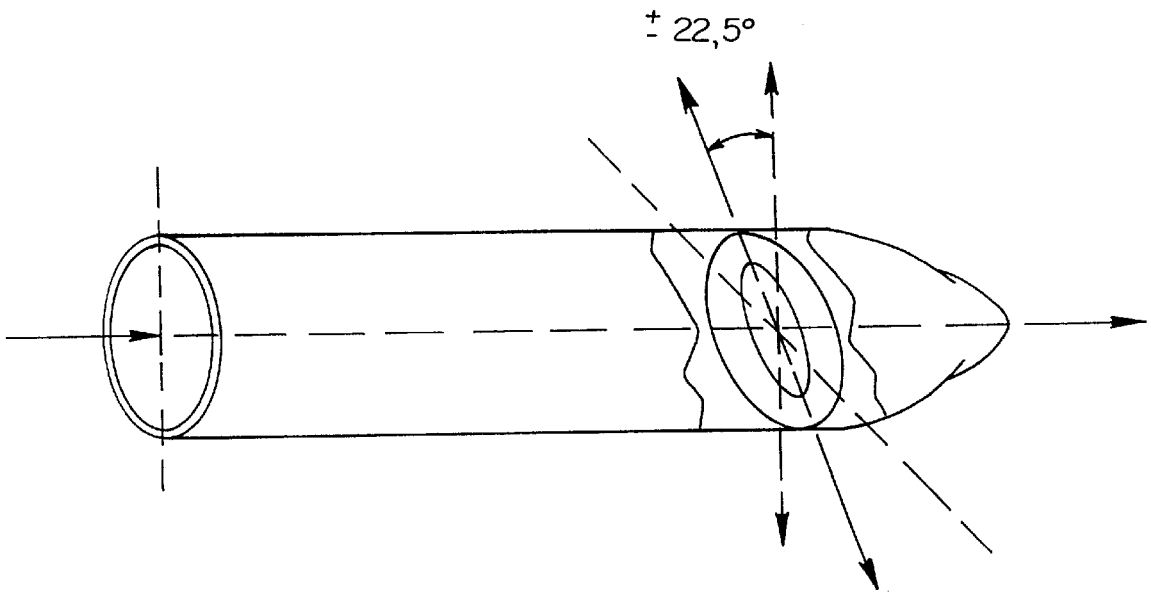
FIG. 3 shows a the view of the condom, object of the present invention, in developed condition, with a value of ($\alpha$) other than 0°.
Figure 4:
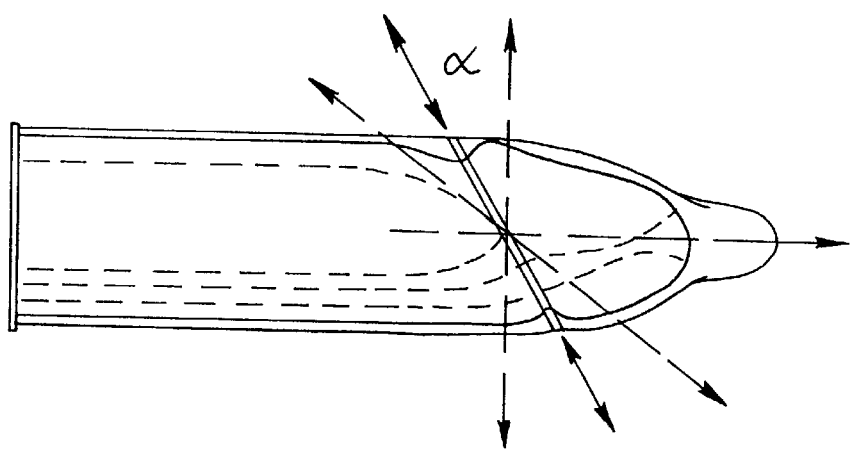
FIG. 4 shows a perspective view of the condom placed on the penis, with the wall or septum inclined, where the ring can be seen with projected inclination.

Its application is simple; when the wall or septum presents an inclination corresponding to the anatomic obliquity of the sulcus and the corona of the glans penis (FIGS. 3 and 4), to carry it out, the body of the condom is unrolled (1) over the penis so that the ring (5) of the septum (4) is fixed onto the sulcus, behind the corona of the glans penis, converting the front chamber (2) into a closed, shut off chamber so that the seminal, fluid inside this cavity (2), upon ejaculation, will not have any back exit. It remains sealed in this front chamber.

The partial or total removal of this new security condom does not occur either even after the penis becomes flaccid, thus avoiding the consequence of spilling seminal fluid or even the loss of the condom (1). All of these characteristics are due to:

The anatomical fixation of the ring the of the septum (4) to the sulcus.

The blocking action of the corona of the glans penis, which prevents the ring (5) from coming off.

The extraction of the condom (1), even once the penis has become flaccid, is to be carried out activity and voluntarily by loosening the condom (1) crossways since, except in case of intended and voluntary action, it is practically impossible that it should be removed accidentally or fortuitously.

In order to apply the condom (1), whose wall is situated with an angle (α), value 0°, that is, perpendicular to the lengthwise axis of the body of the condom (1), the action is the same except that the inclination of this wall or septum (4) is itself created by the action of fitting the condom onto the penis, over the sulcus, since the elasticity of the material the wall (4) is made up of fits onto the sulcus.

In FIG. 7 a form of the safety condom is represented in which the shape that it takes once in position is configured, where the external ring (A) is located at the opening of the condom, its thickness being approximately 1.5 mm. The interior diameter (B) of the back chamber is 35 mm. Within the wall or septum that divides the front and back chambers, the interior diameter (C) is 27 mm., the exterior diameter is 32 mm., and the ring is 2.5 mm thick. This reduces the exterior diameter of the condom by 3 mm.

For all of the above reasons, the new safety condom is a new invention which implies inventive activity and can be applied, with its particular and advantageous characteristics, to the known solutions; it is also subject to fabrication.

It also constitutes an advantageous contribution, both generally as a safety and medically preferable for the prevention of diseases, as wall as related to sexual transmition—S.T.D. and AIDS.

Once the nature of the present invention, new safety condom, has been sufficiently described, it may be subject to modifications both in its makeup and in the materials, colours, dimensions, proportions, etc. used in the whole or part of its components, and in general, any other accessory or secondary details. Therefore, other forms of realisation where secondary changes have been introduced that do not detract from its basic characteristics are not in any way ruled out. On the contrary, the present invention also includes all of its variations, as long as they do not substantially affect the characteristics claimed herefoth.

What is claimed is:

1. A safety condom for general application as contraceptive means and for prevention of sexually transmitted diseases (S.T.D.) and AIDS, the condom having or front compartment and a back compartment which, when the condom is worn by a human penis, are separated and made independent of one another by or septum shaped and integrated in a body of the condom, the septum having an opening ring located concentrically with a circumference that makes up an outer contour of the body of the condom, the opening ring having a diameter smaller than a diameter of the body of the condom and the opening ring being positioned in a plane perpendicular to a lengthwise axis of the body of the condom and longitudinally positioned to engage inside a corona of a glans penis;

wherein the septum shapes a peripheral surface of a back wall of the front compartment and the peripheral surface extends from the opening ring towards a contour of the front compartment of the body of the condom, progressively increasing a diameter of a section of the septum perpendicular to the lengthwise axis of the body of the condom until the diameter is the same as that of the front compartment, so forming a peripheral wall, and the opening ring including in an opening circle a thickening ring that is variable about an entire circular edge of the thickening ring;

wherein a ratio between the diameter of the septum in an area of the opening ring and the diameter of the body of the condom is from about 0.75 to 0.85 in an inner part of the septum and from about 4.85 to 0.95 in an outer part of the septum; and wherein a section diameter of the body of the condom that is perpendicular to the lengthwise axis of the body of the condom is progressively increased from the opening ring towards the back compartment until the section diameter is the same as that of the back compartment.

2. A safety condom in accordance with claim 1, wherein the diameter of the opening ring is smaller than a diameter of an opening of the body of the condom.

3. A safety condom in accordance with claim 1, wherein the septum is situated obliquely in relation to the lengthwise axis of the body of the condom.

4. A safety condom in accordance with the claim 1, wherein an angle of inclination of the septum is between 0° and 45° with respect to the lengthwise axis of the body of the condom, once the condom is applied for use.

5. A safety condom in accordance with claim 4, wherein the inclination of the septum favors a perfect anatomical fixation of the opening ring of the septum onto the inside of the corona of the glans penis, so that an ideal fit is achieved.

* * * * *